United States Patent
Lin

(10) Patent No.: US 10,265,665 B2
(45) Date of Patent: Apr. 23, 2019

(54) HYDROGEN RICH WATER GENERATOR

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 322 days.

(21) Appl. No.: 15/064,516

(22) Filed: Mar. 8, 2016

(65) Prior Publication Data

US 2016/0263535 A1 Sep. 15, 2016

(30) Foreign Application Priority Data

Mar. 9, 2015 (TW) .............................. 104203476 U

(51) Int. Cl.
| | | |
|---|---|---|
| *B01F 3/04* | (2006.01) | |
| *B01F 15/00* | (2006.01) | |
| *A61K 33/00* | (2006.01) | |
| *B01F 11/02* | (2006.01) | |
| *A62D 9/00* | (2006.01) | |

(52) U.S. Cl.
CPC .......... *B01F 3/04978* (2013.01); *A61K 33/00* (2013.01); *B01F 3/04262* (2013.01); *B01F 11/0258* (2013.01); *B01F 15/00857* (2013.01); *A62D 9/00* (2013.01); *B01F 2003/0439* (2013.01); *B01F 2003/04319* (2013.01);
(Continued)

(58) Field of Classification Search
CPC .............. B01F 3/04978; B01F 11/0258; B01F 3/04262; B01F 15/00857; B01F 2003/0439; B01F 2003/04858; B01F 2003/04319; B01F 2003/04914; A61K 33/00; A62D 9/00
See application file for complete search history.

(56) References Cited

U.S. PATENT DOCUMENTS 1,661,659 A * 3/1928 Gray ...................... E04H 12/30
220/560.1
2,134,787 A * 11/1938 Hartman .............. B67D 1/0406
222/146.6
(Continued)

FOREIGN PATENT DOCUMENTS

| CN | 104058544 | * | 9/2014 |
|---|---|---|---|
| JP | 2001104763 A | | 4/2001 |

(Continued)

OTHER PUBLICATIONS

EPO machine translation of JP 2014217813 (Year: 2014).*
(Continued)

*Primary Examiner* — Stephen Hobson
(74) *Attorney, Agent, or Firm* — Foster Pepper PLLC

(57) ABSTRACT

A hydrogen rich water generator includes a container, a hydrogen input, a dividing tube, a vibrator, and a cover. The container is used for containing water and comprises an opening and an inner wall. The hydrogen input is one-piece formed on the inner wall of the container and interconnects the inside and the outside of the container. The dividing tube is configured in the container and connected to the hydrogen input. The vibrator is used for vibrating the water. The cover is configured on the opening of the container wherein when the cover is removed, the water can be added or hydrogen rich water can be taken out. The vibrator of the creation can assist the hydrogen micro bubbles mixed with the water well to generate hydrogen rich water and humidified hydrogen.

9 Claims, 2 Drawing Sheets

(52) U.S. Cl.
CPC .............. *B01F 2003/04858* (2013.01); *B01F 2003/04914* (2013.01)

(56) References Cited

U.S. PATENT DOCUMENTS

| | | | | |
|---|---|---|---|---|
| 3,650,513 | A * | 3/1972 | Werner | B01F 3/04539 261/87 |
| 4,078,985 | A * | 3/1978 | Takeuchi | C25B 9/06 204/228.5 |
| 4,368,060 | A * | 1/1983 | Yanagiako | B01D 53/34 261/124 |
| 4,784,299 | A * | 11/1988 | Stenger | B67D 1/0829 222/397 |
| 8,038,127 | B2 * | 10/2011 | Matsuoka | B01F 3/0446 210/150 |
| 8,460,861 | B2 * | 6/2013 | Satoh | A61M 1/1656 210/634 |
| 8,794,604 | B2 * | 8/2014 | Ryu | B01F 3/04262 261/122.1 |
| 2003/0132104 | A1 * | 7/2003 | Yamashita | C02F 9/00 204/252 |
| 2007/0286795 | A1 * | 12/2007 | Chiba | B62D 61/12 423/580.1 |
| 2008/0311225 | A1 * | 12/2008 | Shiga | C02F 1/4606 424/682 |
| 2010/0201006 | A1 * | 8/2010 | Lee | B01F 3/04078 261/16 |
| 2012/0181711 | A1 * | 7/2012 | Kang | B01F 3/04503 261/4 |
| 2013/0112600 | A1 * | 5/2013 | Satoh | A23L 2/54 210/136 |
| 2014/0268666 | A1 * | 9/2014 | Bretschneider | F21V 33/0036 362/101 |
| 2015/0343399 | A1 * | 12/2015 | Kim | C10L 1/125 435/408 |
| 2017/0259219 | A1 * | 9/2017 | Russell | B01F 5/0465 |
| 2017/0341039 | A1 * | 11/2017 | Minakawa | B01F 3/04836 |

FOREIGN PATENT DOCUMENTS

| | | | |
|---|---|---|---|
| JP | 2005087257 | | 4/2005 |
| JP | 2006289289 | | 10/2006 |
| JP | 2008006365 | A | 1/2008 |
| JP | 2008036331 | * | 2/2008 |
| JP | 2009279241 | | 12/2009 |
| JP | 3166800 | | 3/2011 |
| JP | 2013188668 | | 9/2013 |
| JP | 2014217813 | * | 11/2014 |
| WO | 2015029838 | A1 | 3/2015 |

OTHER PUBLICATIONS

EPO machine translation of CN 104058544 (Year: 2014).*
EPO machine translation of JP2008036331 (Year: 2008).*
Japanese Office Action, dated Jan. 9, 2018, 3 pages.
Japanese Office Action, Application No. 2016045436, dated May 15, 2018, 6 pages.

* cited by examiner

HYDROGEN RICH WATER GENERATOR

FIELD OF THE INVENTION

The present invention relates to a hydrogen rich water generator, and more particularly, to a hydrogen rich water generator for generating humidified hydrogen and hydrogen rich water simultaneously.

DESCRIPTION OF THE PRIOR ART

As people have always been paying much attention on health developments, many developments in medical technology are often targeted on treating diseases and prolonging human life. Also, most of the treatments in the past are passive, which means that the disease is only treated when the disease occurs, and the treatments includes an operation, a medication treatment, a radiation therapy, or a medical treatment for cancer. However, in recent years, most of the medical experts' researches are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and are becoming increasingly popular to the general public.

Free radicals are molecules or ions that have one or multiple unpaired electrons. Free radicals are really active, which means that free radicals are inclined to pull near electrons to join them to be stable. The human body's natural metabolism is a kind of oxidation reaction that produces free radicals spontaneously. Besides, it is necessary to produce many useful chemicals or resist to outside germs for maintaining the normal operation of human body, such as producing enzyme or white blood cell munching on bacteria, and free radicals are produced at the same time. In addition to the above-mentioned internal factors, human body produces extra free radicals due to different kinds of external environment influences, such as bad habits like smoking and excessive drinking, radiation, ultraviolet ray, electromagnetic wave, and even different kinds of environmental pollution. Free radicals attack and damage the cells because of the strong oxidizing power. According to the current study, free radicals are the major cause of a variety of chronic diseases, cancer, and even aging.

The above-mentioned free radicals can be excreted in the form of water by reacting with the inhaled hydrogen because hydrogen is a kind of antioxidant that has strong reducing power. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are clinical experiments showing that for patients who need to inhale a high concentration of oxygen for a long time, the lung damage from the high concentration of oxygen can be ameliorated by inhaling hydrogen. However, hydrogen has to be humidified properly because the structure of the human's tracheal is not suitable for over-dry gas inhalation.

In addition to inhaling humidified hydrogen, the prevention or treatment of diverse disorders can be achieved by drinking or injecting hydrogen rich water, such as hydrogen gas water or hydrogen water. However, the solubility of hydrogen in the water is low. Human body needs to drink or inject a great quantity of hydrogen rich water to achieve better therapeutic effects. Therefore, the goal of this field to be reached is how to generate humidified hydrogen and hydrogen rich water efficiently.

Humidified hydrogen and hydrogen rich water can eliminate free radicals and prevent diseases or resist aging. In addition to be used in hospitals or similar medical units, humidified hydrogen and hydrogen rich water used in daily life can further achieve the effect of early prevention of diseases. In the prior art, the hydrogen rich water generator used in daily life generates water containing hydrogen by electrolyzing water or enabling magnesium to react with water. However, electrolyzing water deposits minerals on the electrode and influences water quality; besides, the reaction of magnesium and water generates the residues of magnesium oxide in water. It is then necessary for these two methods to go through filtering process in order to guarantee the quality of the generated hydrogen rich water. Accordingly, the effects are reduced by the filtering process because part of the hydrogen from hydrogen rich water will effuse to the outside world. Therefore, it is necessary to develop a kind of hydrogen rich water generator used in daily life that has simple procedure and can avoid excessive residues or minerals.

SUMMARY OF THE INVENTION

An object of the present invention is to provide a hydrogen rich water generator includes a container, a hydrogen input, a dividing tube, a vibrator, and a cover. The container is used for containing water and comprises an opening and an inner wall. The hydrogen input is one-piece formed on the inner wall of the container and interconnects the inside and the outside of the container. The dividing tube is configured in the container and connected to the hydrogen input. The vibrator is used for vibrating the water. The cover is configured on the opening of the container wherein when the cover is removed, the water can be added or hydrogen rich water can be taken out. One end of the dividing tube is configured in the container and the other end is connected to the outside of the container, and the tube wall of the dividing tube comprises a plurality of nanometer holes.

The container is used for containing water. One end of the hydrogen input connected to the outside of the container is used to receive hydrogen-containing gas from the outside of the container. The hydrogen-containing gas enters the dividing tube through the hydrogen input and then enters the container through the nanometer holes on the dividing tube to form hydrogen micro bubbles with the water in the container. The vibrator is used for vibrating the water to assist the hydrogen micro bubbles mixed with the water well to generate hydrogen rich water. The hydrogen rich water can be taken out from the container when the cover is removed.

Besides, according to another embodiments of the present invention, the hydrogen rich water generator further comprises a hydrogen output structure, used to collect the humidified hydrogen and output to the outside of the container. Therefore, the hydrogen rich water generator of the present invention can generate hydrogen rich water and humidified hydrogen at the same time, and the procedure is simple. It is not necessary to go through the filtering process for maintaining the hydrogen concentration in the hydrogen rich water.

Another object of the present invention is not only to provide a hydrogen rich water generator having the effect of beauty on the vision, but also for generating hydrogen rich water and humidified hydrogen through simple procedure.

According to another embodiment of the present invention, hydrogen rich water generator further comprises a light-emitting device and the container comprises a transparent side wall. The light-emitting device can glow towards the inside of the container and the light goes through the transparent side wall of the container to be observed by the user on the outside. The light coming from the light-emitting device deflects when reaching the micro bubbles of the hydrogen-containing gas suspended in the water, and forms different visual effects to have the function of beauty.

The advantages and spirits of the invention may be understood by the following recitations together with the appended drawings.

BRIEF DESCRIPTION OF THE DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
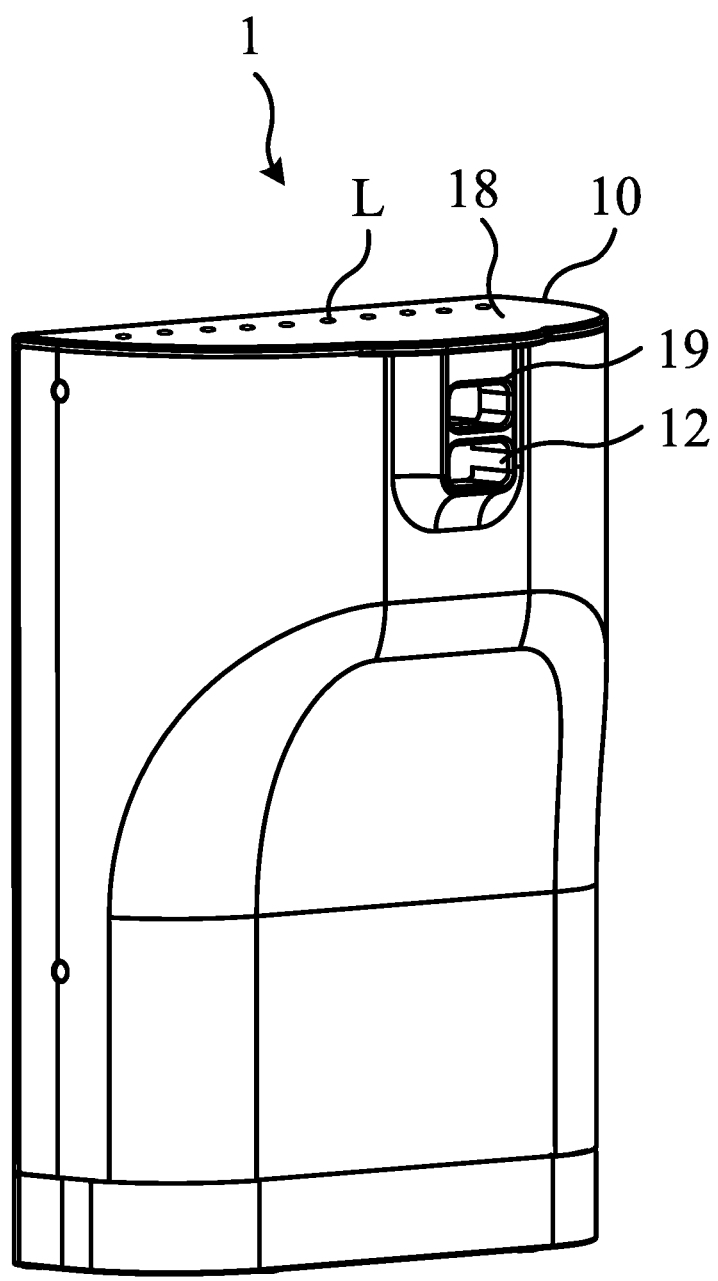
FIG. 1 illustrates the hydrogen rich water generator in an embodiment of the present invention.
Figure 2:
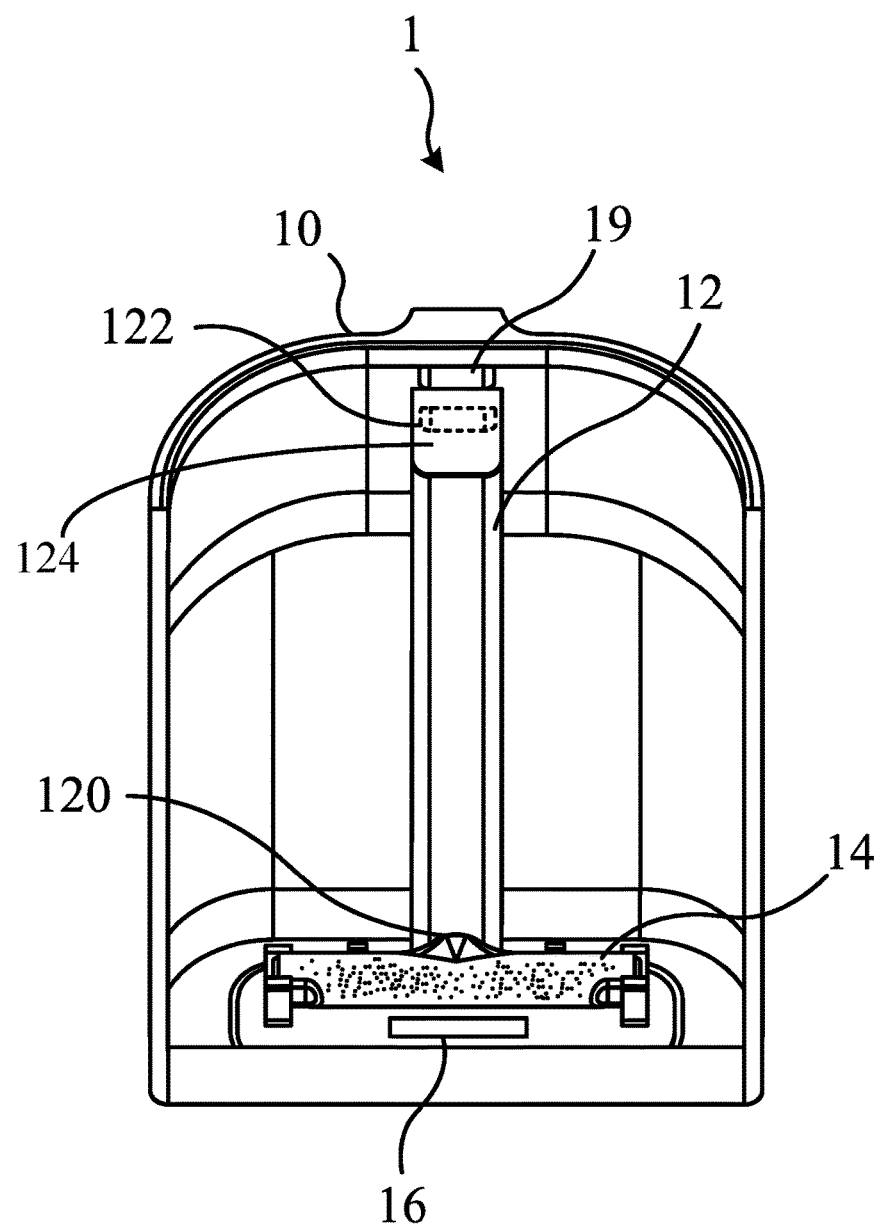
FIG. 2 illustrates the inside construction of the hydrogen rich water generator in an embodiment of the present invention.

Please refer to FIG. 1 and FIG. 2. FIG. 1 shows the hydrogen rich water generator in an embodiment of the present invention. FIG. 2 shows the inside construction of the hydrogen rich water generator in an embodiment of the present invention. Note that the visual angle of FIG. 2 is different from FIG. 1, for showing the inside construction of the hydrogen rich water generator more clearly. As shown in FIG. 1 and FIG. 2, the hydrogen rich water generator comprises a container 10, a hydrogen input 12, a dividing tube 14, a vibrator 16, and a cover 18. The container 10 is used to contain water and comprises an opening and an inner wall. But in the practice application, the container 10 contains, but not limited to, water; it can also be other similar liquid required. In the embodiment of the present invention, the hydrogen input 12 is one-piece formed on the inner wall of the container 10, and comprises a first end 120 extended to the inside of the container or near the bottom of the container and a relative second end 122. The hydrogen input 12 is connected to an external hydrogen generator to receive the hydrogen-containing gas and lead the hydrogen-containing gas to the container 10. The hydrogen-containing gas can be pure hydrogen or gas composed of hydrogen, such as oxygen-hydrogen mixed gas. Furthermore, the second end 122 of the hydrogen input 12 has a plug cover 124, so the hydrogen-containing gas doesn't overflow from the second end 122 and enters the first end 120 as possible as it can. In another embodiment of the present invention, the hydrogen input 12 can also be configured in the container 10 instead of one-piece formed with the container 10.

The first end of the above-mentioned hydrogen input 12 is connected to the central part of the dividing tube 14, so that the received hydrogen-containing gas can enter the dividing tube 14. The tube wall of the dividing tube 14 comprises a plurality of holes for the hydrogen-containing gas to enter the container 10 through the tube wall of the dividing tube 14. Note that, in order to illustrate conveniently, the holes in FIG. 2 are represented by the small holes distributed on the dividing tube 14. Besides, in the embodiment of the present invention, the two ends of the dividing tube 14 are closed, so that the hydrogen-containing gas doesn't escape from these two ends and the water in the container 10 doesn't enter the dividing tube 14. The two ends of the dividing tube 14 in FIG. 2 are closed by two sleeves; however, in the practice application, the two ends of the dividing tube 14 can be closed as a one piece.

Because the container 10 contains water, the hydrogen-containing gas forms hydrogen micro bubbles with the water after entering the container 10 through the dividing tube. The size of the hydrogen micro bubbles is positively correlated to the size of the holes. The holes in the embodiment of the present invention have nanometer scale aperture to reduce the size of the hydrogen micro bubbles effectively. In the practice application, the size of the holes is, but not limited to, between 2 nm to 10 nm; it can also be adjusted according to the need of the user or the designer.

The hydrogen-containing gas forms a large amount of the micro bubbles suspended in the water and moving upward through the plurality of the holes on the dividing tube 14. The micro bubbles carry moisture through the process of moving upward and become humidified. The form of a large amount of micro bubbles raises the contact area of the hydrogen-containing gas and the water substantially and further enhances the degree of humidity. The hydrogen-containing gas is called humidified hydrogen after humidifying. On the other hand, the large amount of micro bubbles formed by the hydrogen-containing gas scatters in the water and effectively improves the solubility of hydrogen in the water to form/generate humidified hydrogen and hydrogen rich water. However, the hydrogen rich water generator of the present invention further comprises a vibrator 16 that can further improve the solubility of hydrogen. The vibrator 16 is configured in the container 10 and vibrates the water in the container 10. As FIG. 2 shows, the vibrator in the embodiment of the present invention is configured on the bottom of the container 10 and comprises an ultrasonic vibrator. The ultrasonic vibrator is used for vibrating the water molecule in the container 10, so that the hydrogen of the hydrogen-containing gas can scatter in the water more effectively. It means that the solubility of hydrogen in the water is increased, and then hydrogen rich water is formed. In the practice application, the vibrator is not only limited to the ultrasonic vibrator in the embodiment of the present invention, and the position is also not limited to the position in FIG. 2. Any kinds of the devices that can be configured on the container and vibrate/stir the water to scatter the hydrogen micro bubbles effectively is all construed as the definition of the vibrator of the present invention. For example, the vibrator can also comprise a centrifuge blade and a driving motor connected to the centrifuge blade. The driving motor is used to drive the centrifuge blade rotating to create turbulence in the water and assist the hydrogen of the hydrogen-containing gas to scatter in the water and to form hydrogen rich water. The vibrator can also comprise all of the above-mentioned ultrasonic vibrators, centrifuge blades, and driving motors to generate the hydrogen rich water more effectively.

Please refer to FIG. 1 again; the hydrogen rich water generator 1 in the embodiment of the present invention further comprises a top cover 18, configured on the top or the opening of the container 10. When the top cover is removed from the container 10, the water can be added or the hydrogen rich water can be taken out from the container 10. Though the top cover 18 on the FIG. 1 can, but not limited to, be removed or be covered on the container 10 in the practice application. Besides, the hydrogen rich water generator 1 can further comprise a sensor (not shown). The sensor starts up the hydrogen generator to generate hydrogen and enter into the hydrogen rich water generator 1 when the hydrogen rich water generator is connected to the hydrogen generator. Otherwise, the sensor shuts down the power of the hydrogen generator to avoid the hydrogen being generated continuously and then overflowed into the air when the hydrogen rich water generator is separated from the hydrogen generator. In an embodiment of the present invention, when the hydrogen rich water generator 1 is embedded with the hydrogen generator, the sensor can be configured on the top cover 18.

In the embodiment of the present invention as FIG. 1 shows, the hydrogen rich water generator 1 further comprises a hydrogen output structure 19 on the hydrogen input 12. As mentioned, the hydrogen-containing gas enters the water and forms the micro bubbles moving upward after going through the holes on the dividing tube 14 and becomes humidified through the process of moving upward. The humidified hydrogen-containing gas moves upward to the top of the container 10, and then be gathered by the hydrogen output structure 19 to be outputted to the outside. The hydrogen output structure 19 can directly provide the humidified hydrogen-containing gas (called as humidified hydrogen) for patients to inhale and can also be connected to handheld or fixed atomized/volatile gas generator, so that the humidified hydrogen-containing gas and the atomized gas generated by the atomized/volatile gas generator form mixed gas for patients to inhale, and the atomized gas can be selected from the group comprising water vapor, atomized liquid, volatile spirits, and the combination thereof. In the embodiment of the present invention, the hydrogen output structure 19 is a gas output configured on the top of the container 10. Due to the high position of the gas output, the hydrogen micro bubbles can be outputted to the outside when moving upward.

In the practice application, the flow rate range of the humidified hydrogen outputted by the hydrogen output structure 19 is between 0.01 L/min and 12 L/min. For example, the flow rate range of the humidified hydrogen is between 1 L/min and 6 L/min cooperating with human respiration. In another embodiment of the present invention, when the top cover is not removed and is covered on the container 10, the hydrogen rich water can be taken out from the hydrogen output structure 19 by inclining the container 10, which is convenient for users' access. Besides, for the convenience of the users to take out the hydrogen rich water, the hydrogen rich water generator 1 can further comprise a hand grip (not shown) for users to grip. The hand grip can be configured on the container, for example, configured on the opposite side of the hydrogen output structure 19 relatively.

In conclusion, the hydrogen rich water generator of the present invention can generate hydrogen rich water and humidified hydrogen-containing gas (or humidified hydrogen) easily, and the generated hydrogen rich water does not contain excessive amounts of minerals or magnesium oxide. Therefore, filtering process is not necessary, and then the solubility remains high.

Furthermore, the container 10 of the present invention hydrogen rich water generator 1 comprises a transparent side wall, and the user can see the inside of the container 10 through the transparent side wall. The position of the transparent side wall can be any one side or plural sides of the FIG. 2 shown, depending on the demand. For example, all the side walls of the container 10 can be transparent such as transparent glass, or just one side wall is transparent and the opposite side wall is laid out a pattern or a particular combination of colors. The user can observe the dividing tube 14 generating a large amount of hydrogen micro bubbles moving upward when the hydrogen-containing gas is received by the hydrogen input 12 and led to the dividing tube 14. Besides, the hydrogen rich water generator 1 in the embodiment of the present invention further comprises a light-emitting device L configured on the top cover 18. The light-emitting device L can glow towards the inside of the container 10 and the light goes through the transparent side wall of the container 10 to be observed by the user. Because a large amount of the hydrogen micro bubbles is in the water of the container 10, the light coming from the light-emitting device L deflects when reaching the micro bubbles, and then forms different visual effects in the container 10 that can be experienced by the user to create the effect of beautification.

The light-emitting device L in the embodiment of the present invention is a LED (light-emitting diode). Various colors of the LED can glow different colors of lights and make the hydrogen rich water generator in the embodiment of the present invention more visual. But in the practice application, the light-emitting device L is not limited to LED, any kinds of the devices that can be configured on the container 10 and glow towards the inside of the container 10 is all construed as the definition of the light-emitting device of the present invention. On the other hand, though the light-emitting device L in FIG. 1 is configured on the top cover 18 of the container 10, it is not limited to this in the practice application; the position can be anywhere that glows towards the inside of the container 10. For example, LED can also be configured on the opaque side wall of the container 10. The different positions of the light-emitting device L can create different visual effects, so the position is set according to the preferences of the users or the designers.

By doing so, the hydrogen rich water generator of the present invention can not only generate hydrogen rich water and humidified hydrogen easily and effectively, but also create visual effects through the light-emitting device glowing towards the micro bubbles in the container, and stimulate purchasing desire of the consumer.

On the other hand, in the embodiment in FIG. 2, the first end 120 of the hydrogen input 12 is connected to the central part of the dividing tube 14, but in the practice application, the first end of the hydrogen input can be connected to the dividing tube in different types, such as locking through a joint. According to another embodiment of the present invention, the central part of the dividing tube of the hydrogen rich water generator does not have an opening that can be connected to the hydrogen input, so it's one end of the dividing tube that is connected to the first end of the hydrogen input, and the tube wall of the dividing tube has holes and the other end is closed. This type of the hydrogen input and the dividing tube can also generate a large amount of hydrogen micro bubbles, and generate hydrogen rich water and humidified hydrogen through the vibrator. In another embodiment of the present invention, for the convenience to configure the hydrogen input 12 on the dividing tube 14, the hydrogen rich water generator 1 further comprises a removal bottom cover (not shown) configured on the bottom of the container 10. Besides, the hydrogen rich water generator 1 can also comprise a connection head (not shown) configured between the bottom cover and the bottom of the container to tighten the joint of the bottom cover and the container 10.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

The embodiments of the invention in which an exclusive property or privilege is claimed are defined as follows:

What is claimed is:

1. A hydrogen rich water generator, comprising:
  a container configured to contain water, wherein the container comprises an opening and an inner wall;
  a hydrogen input, one-piece formed on the inner wall of the container, wherein the hydrogen input comprises a first end configured in the container for receiving hydrogen-containing gas from outside of the container; and
  a dividing tube configured in the container and coupled to the first end of the hydrogen input for receiving the hydrogen-containing gas through the hydrogen input, wherein a tube wall of the dividing tube has a plurality of holes for outputting the hydrogen-containing gas into the water to generate hydrogen rich water and humidified gas;
  wherein the container further comprises a hydrogen output structure configured on the container for outputting the humidified gas to the outside of the container, and the hydrogen output structure is coupled with an atomized/volatile gas generator for mixing the humidified gas with the atomized gas generated by the atomized/volatile gas generator.

2. The hydrogen rich water generator of claim 1, further comprising a light-emitting device, wherein the container comprises a transparent side wall, the light-emitting device is configured on a top cover of the hydrogen rich water generator for lighting inside the container, and light from the light-emitting device goes through the transparent side wall of the container for lighting from the container.

3. The hydrogen rich water generator of claim 2, wherein the light-emitting device is a LED (light-emitting diode).

4. The hydrogen rich water generator of claim 1, further comprising a vibrator, wherein the vibrator comprises an ultrasonic oscillator for vibrating the water in the container.

5. The hydrogen rich water generator of claim 1, further comprising a vibrator, wherein the vibrator comprises a centrifuge blade and a driving motor coupled to the centrifuge blade, and the driving motor is configured to drive the centrifuge blade to vibrate and centrifuge the water in the container.

6. The hydrogen rich water generator of claim 1, wherein the first end of the hydrogen input is coupled to a central part of the dividing tube, and two ends of the dividing tube are closed.

7. The hydrogen rich water generator of claim 1, wherein the hydrogen output structure is configured to output the hydrogen rich water to the outside of the container.

8. The hydrogen rich water generator of claim 7, wherein a flow rate of the humidified gas outputted by the hydrogen output structure is between 0.01 L/min and 12 L/min.

9. The hydrogen rich water generator of claim 1, wherein the size of the plurality of holes is between 2 nm to 10 nm.

* * * * *